United States Patent [19]

Kirino et al.

[11] 4,235,925

[45] Nov. 25, 1980

[54] N-BENZOYLANTHRANILATE DERIVATIVES AS PHYTOPATHOGENIC FUNGICIDAL AGENTS

[75] Inventors: Osamu Kirino, Ashiya; Toshiro Kato, Ibaraki; Shigeo Yamamoto, Ikeda, all of Japan

[73] Assignee: Sumitomo Chemical Company, Limited, Osaka, Japan

[21] Appl. No.: 862,527

[22] Filed: Dec. 20, 1977

[30] Foreign Application Priority Data

Jan. 6, 1977 [JP] Japan ................................. 52-693
Feb. 8, 1977 [JP] Japan ................................. 52-13447
Mar. 10, 1977 [JP] Japan ............................... 52-26727
Jun. 3, 1977 [JP] Japan ................................. 52-65973

[51] Int. Cl.$^3$ ..................... A01N 43/16; A01N 37/10
[52] U.S. Cl. ........................ 424/282; 260/340.5 R; 424/310
[58] Field of Search .................. 424/282, 310; 560/45, 560/47, 48

[56] References Cited

U.S. PATENT DOCUMENTS

| 3,175,950 | 3/1965 | Abraham et al. ................ 560/45 |
| 3,536,723 | 10/1970 | Ghelardoni et al. ............. 560/45 |
| 4,070,484 | 1/1978 | Harita et al. .................... 424/282 |

FOREIGN PATENT DOCUMENTS 917165 12/1972 Canada .
1456246 9/1966 France .
7409M 12/1969 France .

OTHER PUBLICATIONS

Stedman's Medical Dictionary, 18th Rev. Ed., (1953), p. 537.
Chem. Abstracts 81:59113q.
Chem. Abstracts, 1972–1976, Collective Index, p. 6362cs.
Legrand, Bull'n Soc. Chim., France, 1960, pp. 337-342.
Wadge et al., Journ. Chem. Soc. 1956, pp. 4420-4421.
Heindel et al., Journ. Med. Chem., vol. 11, 1968, pp. 369-370.

*Primary Examiner*—Ethel G. Love
*Attorney, Agent, or Firm*—Stevens, Davis, Miller & Mosher

[57] ABSTRACT

A fungicidal composition which comprises as an active ingredient a N-benzoylanthranilate compound of the formula,

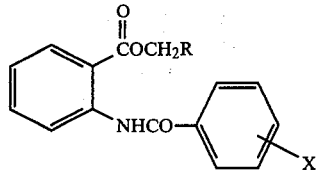

wherein X is a hydrogen or 3-halogen atom or a 3-methoxy, 4-methoxy, 2,4-dimethoxy, 3,4-dimethoxy, 3-halo-4-methoxy, 3,4-methylenedioxy or 3,5-dimethoxy group and R is a hydrogen atom or a $C_1$–$C_7$ alkyl, $C_3$–$C_6$ cycloalkyl, $C_2$–$C_4$ alkenyl, halo-$C_1$–$C_3$ alkyl, $C_1$–$C_4$ alkoxy $C_1$–$C_4$ alkyl or N,N-di-$C_1$–$C_2$ alkylamino $C_1$–$C_4$ alkyl group and an inert carrier, and their preparation and use as a fungicide.

18 Claims, No Drawings

N-BENZOYLANTHRANILATE DERIVATIVES AS PHYTOPATHOGENIC FUNGICIDAL AGENTS

The present invention relates to a fungicidal composition which comprises as an active ingredient a N-benzoylanthranilate compound of the formula,

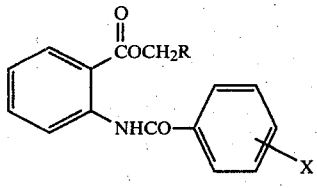

wherein X is a hydrogen or 3-halogen atom (e.g. fluorine, chlorine, bromine, iodine) or a 3-methoxy, 4-methoxy, 2,4-dimethoxy, 3,4-dimethoxy, 3-halo-4-methoxy (e.g. 3-chloro-4-methoxy, 3-fluoro-4-methoxy), 3,4-methylenedioxy or 3,5-dimethoxy group and R is a hydrogen atom or a $C_1$–$C_7$ alkyl, $C_3$–$C_6$ cycloalkyl, $C_2$–$C_4$ alkenyl, halo-$C_1$–$C_3$ alkyl (e.g. chloromethyl), $C_1$–$C_4$ alkoxy $C_1$–$C_4$ alkyl or N,N-di-$C_1$–$C_2$ alkylamino $C_1$–$C_4$ alkyl group and an inert carrier, and their preparation and use as a fungicide.

Some of the N-benzoylanthranilate compounds [I] are per se known [cf. J. Am. Chem. Soc., 62 3136 (1940); J. Chem. Soc., 2471 (1954); J. Chem. Soc., 4420 (1956); Bull. soc. chim. France, 337 (1960)]. However, the fungicidal activity of the N-benzoylanthranilate compounds [I] against a phytopathogenic fungi has never studied.

It has now been found N-benzoylanthranilate compounds [I] have prominent effects on such a wide scope of fungi as *Piriculaira oryzae, Alternaria kikuchiana, Alternaria mali, Venturia inaequalis, Diaporthe citri, Botrytis cinerea, Glomerella cingulata, Sclerotinia cinerea* and *Phytophthora infestans.* They are especially effective in controlling the powdery mildew diseases of agricultural and horticultural crops such as cereals, fruit crops, vegetables and ornamental plants which are caused by the phytopathogenic fungi such as *Podosphaera leucotricha, Phyllactinia pyri, Phyllactinia kakicola, Uncinula necator, Sphaerotheca funliginea, Erysiphe cichoracearum, Sphaerotheca pannosa, Sphaerotheca humuli, Erysiphe graminis* f. sp. *hordei* and *Erysiphe graminis* f. sp. *tritici.* Recently, the emergence of plant pathogens resistant to fungicides has been often noticed in fields, becoming a serious practical problem in crop protection with fungicide application. The N-benzoylanthranilate compounds [I] were found to exhibit a strong fungitoxicity towards those fungicide-resistant pathogens. For example, they have the same fungitoxic activity on the Benomyl-resistant strain of *Sphaerotheca fuliginea* and *Erysiphe cichoracearum* [Ann. Rev. Phytopathology, 14, 405 (1976)] as on the respective wild strains (susceptible strains). It can be therefore expected that N-benzoylanthranilate compounds [I] exert prominent controlling effect on plant diseases in the fields where fungicide-resistant pathogens have already emerged. Advantageously, they are extremely low in toxicity and have little detrimental actions on mammals and fish.

The N-benzoylanthranilate compounds [I] of the present invention structurally relate to some of the compounds disclosed in the literature [J. Med. Chem., 11, 369 (1968)], but their effectivenesses in controlling the powdery mildew diseases are superior to those of the latter compounds, and the N-benzoylanthranilate compounds [I] are still effective with application at lower dosages.

A main object of the present invention is to provide fungicidal compositions containing such N-benzoylanthranilate compounds [I], which are useful as fungicides. Another object of this invention is to provide novel N-benzoylanthranilate compounds [I'] of the formula as shown below which are an active ingredient of said fungicidal compositions. A further object of this invention is to provide a process for producing such N-benzoylanthranilate compounds [I']. These and other objects and advantages of the invention will become apparent from the foregoing and subsequent descriptions.

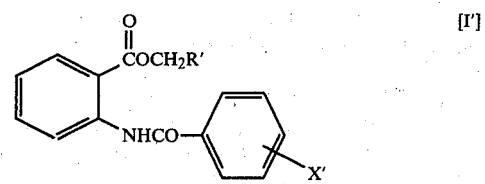

wherein X' is a hydrogen or 3-halogen atom (e.g. fluorine, chlorine, bromine, iodine) or a 4-methoxy, 2,4-dimethoxy, 3,4-dimethoxy, 3,4-methylenedioxy or 3,5-dimethoxy group and R' is a $C_2$–$C_7$ alkyl, $C_3$–$C_6$ cycloalkyl, $C_2$–$C_4$ alkenyl, halo-$C_1$–$C_3$ alkyl (e.g. chloromethyl) or N,N-di-$C_1$–$C_2$ alkylamino $C_1$–$C_4$ alkyl group.

The N-benzoylanthranilate compounds [I] can be prepared by reacting an anthranilate of the formula,

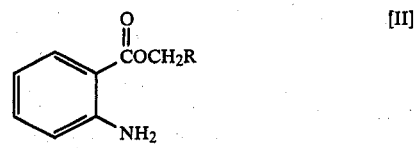

wherein R is as defined above, with a benzoyl chloride of the formula,

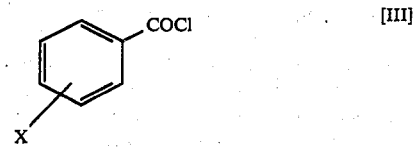

wherein X is as defined above.

The reaction is usually carried out by stirring a mixture of the starting anthranilate compound [II] with an equivalent or excess molar amount of the benzoyl chloride [III] at room temperature (0°–35° C.) in the presence or absence of an inert solvent (e.g. benzene, toluene, xylene, tetrahydrofuran, dioxane, chlorobenzene, chloroform, carbon tetrachloride, nitrobenzene, water, methanol, ethanol, methyl isobutyl ketone, acetone, methylene dichloride, dichloroethane). When desired, the reaction may be performed while heating (up to reflux) and/or in the presence of a dehydrochlorinating agent (e.g. pyridine, triethylamine, quinoline, N,N-dimethylaniline, N,N-diethylaniline, N-methylmorpholine, sodium methylate, sodium ethylate, sodium hydroxide, sodium amide) so as to accomplish the production of the objective compound smoothly. The N-benzoylanthranilate compound [I] thus produced may be purified, if necessary, by a per se conventional procedure such as recrystallization, distillation and/or column chromatography.

The preferable N-benzoylanthranilate compounds [I] as an active ingredient of the fungicidal composition of the present invention are those having the general formula [I] wherein X is a hydrogen, 3-fluorine, 3-chlorine, 3-bromine or 3-iodine atom or a 3-methoxy, 4-methoxy, 2,4-dimethoxy, 3,4-dimethoxy, 3-fluorine-4-methoxy, 3-chlorine-4-methoxy, 3,4-methylenedioxy or 3,5-dimethoxy group and R is a hydrogen atom or a $C_1$–$C_7$ alkyl, cyclopropyl, vinyl, 2-methylvinyl, chloromethyl, methoxymethyl or N,N-dimethylaminomethyl group; and the more preferable N-benzoylanthranilate compounds [I] are those having the general formula [I] wherein X is a hydrogen atom and R is a hydrogen atom or a methyl or vinyl group; those having the general formula [I] wherein X is a 3-iodine atom and R is a methyl, ethyl, n-propyl, vinyl, chloromethyl or N,N-dimethylaminomethyl group; those having the general formula [I] wherein X is a 4-methoxy group and R is an ethyl, i-propyl or vinyl group; those having the general formula [I] wherein X is a 3,4-dimethoxy group and R is a hydrogen atom or a methyl, ethyl, n-propyl, i-propyl, vinyl, methoxymethyl or N,N-dimethylaminomethyl group; and those having the general formula [I] wherein X is a 3,4-methylenedioxy group and R is a hydrogen atom or a methyl, ethyl, n-propyl or methoxymethyl group.

In actual application as fungicides, the N-benzoylanthranilate compounds [I] may be used alone without incorporation of any other ingredients such as carriers and diluents or, for easier application, in admixture with such solid carriers or diluents as talc, clay and the like or with such liquid carriers or diluents as organic solvents and the like. The fungicidal compositions can be formulated into any of ordinarily adopted forms such as, for example, dusts, wettable powders, oil sprays, aerosols, tablets, emulsifiable concentrates and granules.

The foregoing preparations generally contain 1.0 to 95.0% by weight, preferably 2.0 to 80.0% by weight of the active ingredient (including other ingredients mixed). A suitable amount of the preparations applied is generally 10 g to 1000 g/10 are, and the concentration of the preparations applied is preferably within the range of 0.01 to 0.5% by weight. Since, however, the amount and concentration depend upon the preparation forms, application times, application methods, application sites, diseases and crops, they may be properly increased or decreased irrespective of the aforesaid ranges.

Further, the N-benzoylanthanilate compounds [I] may be used in admixture with other funcidies such as, for example, N-(3,5-dichlorophenyl9-1,2-dimethylcyclopropane-1,2-dicarboximide, S-n-butyl-S'-p-tert-butylbenzyl-N-3-pyridyldithiocarbonimidate, O,O-dimethyl-O-2,6-dichloro-4-methylphenylphosphorothioate, methyl 1-(butylcarbamoyl)-2-benzimidazolecarbamate, N-trichloromethylthio-4-cyclohexene-1,2-dicarboximide, cis-N-(1,1,2,2-tetrachloroethylthio)-4-cyclohexene-1,2-dicarboximide, Polyoxyin, Streptomycin, zinc ethylene-bis(dithiocarbamate), zinc dimethylthiocarbamate, manganese ethylene-bis(dithiocarbamate), bis(dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene and the like; and the N-benzoylanthranilate compounds [I] also may be used in admixture with insecticides such as, for example, O,O-dimethyl-O-(4-nitro-m-tolyl)phosphorothioate, O-p-cyanophenyl-O,O-dimethylphosphorothioate, O-p-cyanophenyl-O-ethylphenylphosphonothioate, O,O-dimethyl-S-(N-methylcarbamoylmethyl)phosphorodithioate, 2-methoxy-4H-1,3,2-benzodioxaphosphorine-2-sulfide, O,O-dimethyl-S'-(1-ethoxycarbonyl-1-phenylmethyl)phosphorodithioate, α-cyano-3-phenoxybenzyl-2-(4-chlorophenyl)isovalerate, 3-phenoxybenzyl-2,2-dimethyl-3-(2,2-dichlorovinyl)cyclopropanecarboxylate, 3-phenoxybenzyl chrysanthemate and the like; and, in every case, no controlling effects of individual chemicals are decreased. Accordingly, simultaneous control of two or more injurious fungi and insects is possible. In addition, they may be used in admixture with such agricultural chemicals as nematocides and miticides and with fertilizers.

Practical and presently preferred embodiments of the present invention are illustratively shown in the following examples, wherein parts and % are by weight.

EXAMPLE 1

Preparation of the N-benzoylanthranilate compounds [I]:

One tenth mole of an anthranilate of the formula [II] and 0.11 mole of triethylamine were dissolved in 200 ml of benzene, and 0.1 mole of benzoyl chloride of the formula [III] was added thereto dropwise slowly at room temperature with stirring. After the addition was finished, the mixture was heated under reflux for 2 hours. The reaction mixture was filtered, and the filtrate was concentrated under reduced pressure. The residue obtained was recrystallized from an ethanol to obtain the objective N-benzoylanthranilate compounds of the formula [I] in a high yield.

According to the above procedure, the N-benzoylanthranilate compounds [I] as shown in Table 1 were prepared.

Table 1

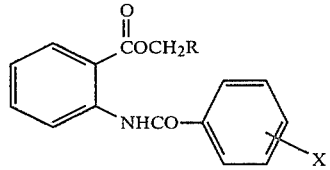

| Compound No. | X | R | Physical Constant | Elementary analysis | | | | | | | |
|---|---|---|---|---|---|---|---|---|---|---|---|
| | | | | Calcd. (%) | | | | Found (%) | | | |
| | | | | C | H | N | Halogen | C | H | N | Halogen |
| 1 | H | H | mp 101°–102° C. | 70.58 | 5.13 | 5.49 | — | 70.47 | 5.02 | 5.61 | — |

Table 1-continued

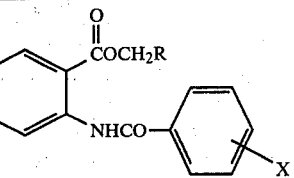

| Compound No. | X | R | Physical Constant | Calcd. (%) C | H | N | Halogen | Found (%) C | H | N | Halogen |
|---|---|---|---|---|---|---|---|---|---|---|---|
| 2 | 3-F | " | mp 104°–105.5° C. | 65.93 | 4.43 | 5.13 | — | 65.91 | 4.43 | 5.04 | — |
| 3 | 3-Cl | " | mp 98°–99° C. | 62.19 | 4.18 | 4.83 | 12.24 (Cl) | 62.18 | 4.17 | 4.80 | 12.43 (Cl) |
| 4 | 3-Br | " | mp 90°–91° C. | 53.91 | 3.62 | 4.19 | 23.91 (Br) | 53.89 | 3.52 | 4.18 | 24.00 (Br) |
| 5 | 3-I | " | mp 86°–87° C. | 47.27 | 3.17 | 3.67 | 33.29 (I) | 47.16 | 3.07 | 3.71 | 33.11 (I) |
| 6 | 3-CH$_3$O | " | mp 86°–87° C. | 67.36 | 5.30 | 4.91 | — | 67.42 | 5.34 | 4.85 | — |
| 7 | 4-CH$_3$O | " | mp 113.5°–114.5° C. | 67.36 | 5.30 | 4.91 | — | 67.39 | 5.35 | 4.89 | — |
| 8 | 2,4-(CH$_3$O)$_2$ | " | mp 98°–99° C. | 64.75 | 5.43 | 4.44 | — | 64.64 | 5.50 | 4.35 | — |
| 9 | 3,4-(CH$_3$O)$_2$ | H | mp 109°–110° C. | 64.75 | 5.43 | 4.44 | — | 64.80 | 5.52 | 4.27 | — |
| 10 | 3-F, 4-CH$_3$O | " | mp 157°–158° C. | 62.28 | 4.18 | 4.84 | — | 62.35 | 4.07 | 4.67 | — |
| 11 | 3-Cl, 4-CH$_3$O | " | mp 134°–135° C. | 60.11 | 4.41 | 4.38 | 11.09 (Cl) | 59.86 | 4.25 | 4.23 | 11.25 (Cl) |
| 12 | 3,4-OCH$_2$O— | " | mp 164°–165° C. | 64.21 | 4.38 | 4.68 | — | 64.25 | 4.43 | 4.64 | — |
| 13 | H | —CH$_3$ | mp 103°–104° C. | 71.36 | 5.61 | 5.20 | — | 71.32 | 5.64 | 4.07 | — |
| 14 | 3-I | " | mp 116.5°–117.5° C. | 48.63 | 3.57 | 3.54 | 32.11 (I) | 48.59 | 3.54 | 3.71 | 31.95 (I) |
| 15 | 4-CH$_3$O | " | mp 117°–118° C. | 68.22 | 5.72 | 4.68 | — | 68.01 | 5.73 | 4.70 | — |
| 16 | 2,4-(CH$_3$O)$_2$ | " | mp 91°–92° C. | 65.64 | 5.81 | 4.25 | — | 65.55 | 5.82 | 4.31 | — |
| 17 | 3,4-(CH$_3$O)$_2$ | " | mp 110°–111° C. | 65.64 | 5.81 | 4.25 | — | 65.68 | 5.93 | 4.20 | — |
| 18 | 3,4-OCH$_2$O— | " | mp 108°–109° C. | 65.17 | 4.83 | 4.47 | — | 64.99 | 4.78 | 4.53 | — |
| 19 | H | —CH$_2$CH$_3$ | mp 84°–85° C. | 72.07 | 6.05 | 4.94 | — | 72.28 | 6.01 | 4.80 | — |
| 20 | 3-I | " | mp 95.5°–97° C. | 49.90 | 3.94 | 3.42 | 31.01 (I) | 49.71 3.83 | 3.27 | 31.22 (I) | |
| 21 | 4-CH$_3$O | " | mp 76°–77° C. | 69.00 | 6.11 | 4.47 | — | 68.82 | 6.03 | 4.36 | — |
| 22 | 3,4-(CH$_3$O)$_2$ | " | mp 89°–90° C. | 66.46 | 6.16 | 4.08 | — | 66.41 | 6.14 | 3.99 | — |
| 23 | 3,4-OCH$_2$O— | " | mp 101°–102° C. | 66.05 | 5.23 | 4.28 | — | 65.89 | 5.27 | 4.11 | — |
| 24 | 3-I | —CH$_2$CH$_2$CH$_3$ | mp 85°–86° C. | 51.08 | 4.29 | 3.31 | 29.98 (I) | 51.05 | 4.17 | 3.36 | 30.13 (I) |
| 25 | 2,4-(CH$_3$O)$_2$ | —CH$_2$CH$_2$CH$_3$ | mp 55°–56° C. | 67.21 | 6.49 | 3.92 | — | 67.00 | 6.30 | 4.18 | — |
| 26 | 3,4-(CH$_3$O)$_2$ | " | mp 91°–92° C. | 67.21 | 6.49 | 3.92 | — | 67.18 | 6.45 | 4.09 | — |
| 27 | 3,4-OCH$_2$O— | " | mp 92°–93° C. | 66.85 | 5.61 | 4.10 | — | 66.69 | 5.71 | 4.33 | — |
| 28 | 3,5-(CH$_3$O)$_2$ | " | mp 89°–90° C. | 67.21 | 6.49 | 3.92 | — | 67.03 | 6.54 | 3.98 | — |
| 29 | 4-CH$_3$O | —CH(CH$_3$)$_2$ | mp 76°–77° C. | 69.71 | 6.47 | 4.28 | — | 69.65 | 6.45 | 4.30 | — |
| 30 | 3,4-(CH$_3$O)$_2$ | " | mp 87.5°–89° C. | 67.21 | 6.49 | 3.92 | — | 67.23 | 6.46 | 4.00 | — |
| 31 | 3-I | —(CH$_2$)$_3$CH$_3$ | mp 57°–58.5° C. | 52.19 | 4.61 | 3.20 | 29.02 (I) | 52.03 | 4.05 | 3.04 | 29.31 (I) |
| 32 | 3,4-(CH$_3$O)$_2$ | " | mp 75.5°–76.5° C. | 67.91 | 6.78 | 3.77 | — | 67.87 | 6.82 | 3.80 | — |
| 33 | 3,4-OCH$_2$O— | " | mp 94.5°–95.5° C. | 67.59 | 5.96 | 3.94 | — | 67.58 | 6.00 | 3.85 | — |
| 34 | 3,4-(CH$_3$O)$_2$ | —C(CH$_3$)$_3$ | mp 120°–121° C. | 67.91 | 6.78 | 3.77 | — | 67.87 | 6.79 | 3.71 | — |
| 35 | 3-I | —(CH$_2$)$_4$C$_3$ | mp 60°–61.5° C. | 53.23 | 4.91 | 3.10 | 28.12 (I) | 53.20 | 4.68 | 3.05 | 28.33 (I) |
| 36 | 3,4-(CH$_3$O)$_2$ | " | mp 90°–91° C. | 68.55 | 7.06 | 3.63 | — | 68.64 | 7.07 | 3.63 | — |
| 37 | 3,4-OCH$_2$O— | " | mp 61°–62° C. | 68.28 | 6.28 | 3.79 | — | 68.35 | 6.25 | 3.82 | — |
| 38 | 3,4-(CH$_3$O)$_2$ | C$_2$H$_5$<br>\|<br>—CH(CH$_2$)$_3$CH$_3$ | n$_D^{25.5}$ 1.5761 | 69.71 | 7.56 | 3.39 | — | 69.58 | 7.72 | 3.21 | — |
| 39 | 3-I | ◁ | mp 136°–137° C. | 51.33 | 3.83 | 3.33 | 30.13 (I) | 51.37 | 3.38 | 3.40 | 30.25 (I) |
| 40 | H | —CH=CH$_2$ | mp 65.5°–66.5° C. | 72.58 | 5.37 | 4.98 | — | 72.58 | 5.24 | 4.94 | — |
| 41 | 3-I | " | mp 70°–71.5° C. | 50.14 | 3.47 | 3.44 | 31.16 (I) | 49.95 | 3.29 | 3.46 | 31.30 (I) |
| 42 | 4-CH$_3$O | " | mp 91°–92° C. | 69.45 | 5.50 | 4.50 | — | 69.61 | 5.45 | 4.58 | — |
| 43 | 3,4-(CH$_3$O)$_2$ | " | mp 100°–101° C. | 66.85 | 5.61 | 4.10 | — | 67.13 | 5.54 | 4.38 | — |
| 44 | 3,4-OCH$_2$O— | " | mp 115.5°–116.5° C. | 66.46 | 4.65 | 4.31 | — | 66.35 | 4.61 | 4.43 | — |
| 45 | 3-I | —CH=CH—CH$_3$ | mp 79°–81° C. | 51.33 | 3.83 | 3.33 | 30.13 (I) | 51.08 | 3.61 | 3.26 | 30.42 (I) |
| 46 | 3,4-OCH$_2$O— | " | mp 94°–95° C. | 67.25 | 5.05 | 4.13 | — | 67.03 | 4.95 | 3.92 | — |
| 47 | 3-I | —CH$_2$Cl | mp 103.5°–105° C. | 44.73 | 3.05 | 3.26 | 29.54 (I) 8.25 (Cl) | 44.59 | 2.98 | 3.34 | 29.65 (I) 8.37 (Cl) |
| 48 | H | —CH$_2$OCH$_3$ | mp 105°–106° C. | 68.22 | 5.72 | 4.68 | — | 68.25 | 5.81 | 4.77 | — |
| 49 | 3,4-(CH$_3$O)$_2$ | " | mp 96.5°–97.5° C. | 63.50 | 5.89 | 3.90 | — | 63.75 | 5.85 | 4.19 | — |
| 50 | 3,4-OCH$_2$O— | " | mp 102°–104° C. | 62.97 | 4.99 | 4.08 | — | 63.12 | 5.20 | 3.95 | — |
| 51 | 3-I | —CH$_2$N(CH$_3$)$_2$ | mp 65°–66° C. | 49.33 | 4.37 | 6.39 | 28.96 (I) | 49.35 | 4.21 | 6.52 | 28.77 (I) |
| 52 | 3,4-(CH$_3$O)$_2$ | " | mp 96°–97° C. | 64.50 | 6.50 | 7.52 | — | 64.44 | 6.43 | 6.30 | — |

EXAMPLE 2

Formulation of compositions:

(a) Dust

2 Parts of the compound (14) and 98 parts of clay were thoroughly pulverized and mixed together to obtain a dust containing 2% of the active ingredient. In application, the dust was dusted as such.

(b) Dust

3 Parts of the compound (27) and 97 parts of talc were thoroughly pulverized and mixed together to obtain a dust containing 3% of the active ingredient. In application, the dust was dusted as such.

(c) Wettable powder

50 Parts of the compound (1), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

(d) Wettable powder

80 Parts of the compound (17), 8 parts of a wetting agent of the alkylbenzenesulfonate type and 12 parts of diatomaceous earth were thrughly pulverized and mixed together to obtain a wettable powder containing 80% of the active ingredient. In application, the wettable powder was diluted with water, and the resulting solution was sprayed.

(e) Emulsifiable concentrate

10 Parts of the compound (49), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

(f) Granule 5 parts of the compound (43), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the N-benzoylanthranilate compounds [I]. In these examples, the compound numbers correspond to those in Table 1.

EXAMPLE 3

Protective activity test on powdery mildew of cucumber (*Sphaerotheca fuliginea*)

When cucumber (var.: Sagami-hanjiro) was grown up to a first true leaf stage in a flower pot of 9 cm in diameter, the true leaves were picked off and an aqueous solution of each emulsifiable concentrate was sprayed on the cotyledon at a rate of 10 ml per pot. After 1 day, the cucumber was inoculated by spraying the spore suspension of *Sphaerotheca fuliginea*. After further 14 days, the infectious state was observed. The disease severity was calculated by the following method: The leaves examined were measured for a percentage of infected area and classified into the corresponding disease indices, 0, 1, 2, 3, 4, 5; the leaves belonging to the same disease indices were summed up; and the disease severity was calculated according to the following equation.

| Disease index | Infectious state |
|---|---|
| 0 | No colony on leaf surface |
| 1 | Colony of less than 10% on leaf surface |
| 2 | Colony of less than 30% on leaf surface |
| 3 | Colony of less than 60% on leaf surface |
| 4 | Colony of less than 95% on leaf surface |
| 5 | Colony of not less than 95% on leaf surface |

| Disease index | Infectious state |
|---|---|

$$\text{Disease severity} = \frac{\Sigma(\text{Disease index} \times \text{number of leaves})}{5 \times (\text{Total number of leaves examined})} \times 100$$

The test results are shown in Table 2. The compounds of the present invention showed a more superior protective activity than the control compounds, as is apparent from the test results.

Table 2

| Compound No. | Concentration of active ingredient (ppm) | Disease severity (%) |
|---|---|---|
| 1 | 50 | 0.0 |
| 2 | " | 2.0 |
| 3 | " | 0.0 |
| 4 | " | 1.0 |
| 5 | " | 0.0 |
| 6 | " | 1.0 |
| 7 | " | 0.0 |
| 8 | " | 0.0 |
| 9 | " | 0.0 |
| 10 | " | 0.0 |
| 11 | " | 0.0 |
| 12 | " | 0.0 |
| 13 | " | 1.0 |
| 14 | " | 0.0 |
| 15 | " | 0.0 |
| 16 | " | 0.0 |
| 17 | " | 0.0 |
| 18 | " | 0.0 |
| 19 | " | 2.0 |
| 20 | " | 0.0 |
| 21 | " | 1.0 |
| 22 | " | 0.0 |
| 23 | " | 0.0 |
| 24 | " | 0.0 |
| 25 | " | 1.0 |
| 26 | " | 0.0 |
| 27 | " | 0.0 |
| 28 | " | 1.0 |
| 29 | " | 1.0 |
| 30 | " | 1.0 |
| 31 | " | 2.0 |
| 32 | " | 0.0 |
| 33 | " | 0.0 |
| 34 | " | 2.5 |
| 35 | " | 1.0 |
| 36 | " | 0.0 |
| 37 | " | 0.0 |
| 38 | " | 3.0 |
| 39 | " | 1.0 |
| 40 | " | 0.0 |
| 41 | " | 0.0 |
| 42 | " | 1.0 |
| 43 | " | 0.0 |
| 44 | " | 0.0 |
| 45 | " | 2.0 |
| 46 | " | 1.0 |
| 47 | " | 0.0 |
| 48 | " | 1.0 |
| 49 | " | 0.0 |
| 50 | " | 0.0 |
| 51 | " | 0.0 |
| 52 | " | 0.0 |
| 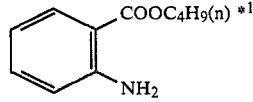 *1 | " | 100.0 |
| 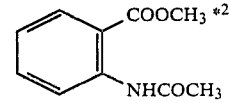 *2 | " | 100.0 |

Table 2-continued

| Compound No. | Concentration of active ingredient (ppm) | Disease severity (%) |
|---|---|---|
| ![structure: COOH, NHCO-phenyl] *3 | " | 100.0 |
| ![structure: COOCH3, NHCO-phenyl-CH3] *3 | " | 100.0 |
| ![structure: COOC2H5, NHCO-phenyl-Br] *3 | " | 100.0 |
| ![structure: COOCH3, NHCO-phenyl-Br] *3 | " | 98.0 |
| ![structure: CH3, CONH-phenyl] *4 | " | 100.0 |
| ![structure: OH, CONH-phenyl] *5 | " | 100.0 |
| ![structure: CONHC4H9, N, NHCOOCH3, N] *6 | " | 7.5 |
| No treatment | — | 100.0 |

Note:
*1 Compound disclosed in J. Med. Chem., Vol. 11, 369 (1968)
*2 Compound disclosed in Can. J. Chem., Vol. 46, 2589 (1968)
*3 Compounds disclosed in Bull. soc. chim. France, 337 (1960)
*4 Commercially available fungicide: mebenil
*5 Commercially available fungicide: salicylanilide
*6 Commercially available fungicide: benomyl

EXAMPLE 4

Protective activity test on pesticides-resistant pathogens:

A protective activity test on powdery mildew of cucumber (*Sphaerotheca fuliginea*) was carried out in the same manner as in Example 3, using *Sphaerotheca fuliginea* resistant to methyl 1-(butylcarbamoyl)-2-benzimidazolecarbamate. The investigation of infection and the calculation of disease severity were carried out in the same manner as in Example 3.

The test results are shown in Table 3. As is apparent from a comparison between the test results of this example and Example 3, the control compound, benomyl[methyl 1-(butylcarbamoyl)-2-benzimidazolecarbamate] displays a controlling effect on the wild strains (susceptible strains), but it has little or no controlling effect on the pesticides-resistant strains. The compounds of the present invention display a strong controlling effect on the pesticides-resistant strains as well as on the susceptible strains.

Table 3

| Compound No. | Concentration of active ingredient (ppm) | Disease severity (%) |
|---|---|---|
| 1 | 50 | 0.0 |
| 5 | " | 0.0 |
| 8 | " | 1.0 |
| 14 | " | 0.0 |
| 18 | " | 0.0 |
| 21 | " | 2.0 |
| 22 | " | 1.0 |
| 23 | " | 0.0 |
| 24 | " | 0.0 |
| 26 | " | 0.0 |
| 27 | " | 0.0 |
| 40 | " | 0.0 |
| 43 | " | 1.0 |
| 49 | " | 1.0 |
| 50 | " | 0.0 |
| 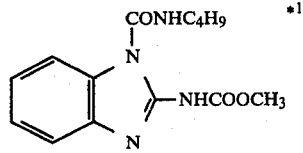 *1 | " | 95.0 |
| No treatment | — | 100.0 |

Note:
*1 Commercially available fungicide: benomyl

EXAMPLE 5

Protective activity test on powdery mildew of barley (*Erysiphe graminis*)

When barley (var.: Akashinriki) was grown up to a first true leaf stage in a flower pot of 9 cm in diameter, an aqueous solution of each emulsifiable concentrate was sprayed on the leaves at a rate of 10 ml of per pot. After the solution was air-dried, the barley was inoculated with *Erysiphe graminis* and cultivated for 10 days under a fluorescent light at 180° C. Thereafter, the infectious state was observed. The investigation of infection and the calculation of disease severity were carried out in the same manner as in Example 3.

The test results are shown in Table 4. As is apparent from the results, the compounds of the present invention showed a more superior protective activity than the control compounds.

Table 4

| Compound No. | Concentration of active ingredient (ppm) | Disease severity (%) |
|---|---|---|
| 1 | 50 | 0.0 |
|   | 10 | 0.0 |
| 5 | 50 | 0.0 |
|   | 10 | 0.5 |
| 7 | 50 | 1.0 |
|   | 10 | 2.0 |
| 8 | 50 | 0.0 |
|   | 10 | 0.5 |
| 9 | 50 | 0.0 |
|   | 10 | 0.0 |
| 12 | 50 | 0.0 |
|   | 10 | 1.0 |
| 14 | 50 | 0.0 |

Table 4-continued

| Compound No. | Concentration of active ingredient (ppm) | Disease severity (%) |
|---|---|---|
| | 10 | 0.0 |
| 17 | 50 | 0.0 |
| | 10 | 0.0 |
| 18 | 50 | 0.0 |
| | 10 | 0.0 |
| 20 | 50 | 0.0 |
| | 10 | 0.5 |
| 22 | 50 | 0.0 |
| | 10 | 1.0 |
| 23 | 50 | 0.0 |
| | 10 | 0.0 |
| 24 | 50 | 0.0 |
| | 10 | 0.0 |
| 25 | 50 | 1.5 |
| | 10 | 3.0 |
| 26 | 50 | 0.0 |
| | 10 | 0.0 |
| 27 | 50 | 0.0 |
| | 10 | 0.0 |
| 28 | 50 | 0.5 |
| | 10 | 3.0 |
| 29 | 50 | 1.0 |
| | 10 | 2.0 |
| 30 | 50 | 1.0 |
| | 10 | 1.5 |
| 36 | 50 | 0.0 |
| | 10 | 0.5 |
| 37 | 50 | 0.0 |
| | 10 | 0.0 |
| 40 | 50 | 0.0 |
| | 10 | 0.0 |
| 42 | 50 | 1.0 |
| | 10 | 3.0 |
| 43 | 50 | 0.0 |
| | 10 | 0.0 |
| 44 | 50 | 0.0 |
| | 10 | 0.0 |
| 45 | 50 | 2.5 |
| | 10 | 6.5 |
| 47 | 50 | 0.0 |
| | 10 | 0.5 |
| 48 | 50 | 1.0 |
| | 10 | 2.5 |
| 49 | 50 | 0.0 |
| | 10 | 0.0 |
| 50 | 50 | 0.0 |
| | 10 | 0.5 |
| [structure: 2-NH$_2$-C$_6$H$_4$-COOC$_4$H$_9$(n)] *1 | 50 | 100.0 |
| [structure: 2-NHCOCH$_3$-C$_6$H$_4$-COOCH$_3$] *2 | " | 100.0 |
| [structure: 2-(NHCO-C$_6$H$_5$)-C$_6$H$_4$-COOH] *3 | " | 100.0 |
| [structure: 2-(NHCO-C$_6$H$_4$-CH$_3$-p)-C$_6$H$_4$-COOCH$_3$] *3 | " | 100.0 |
| [structure: 2-(NHCO-C$_6$H$_4$-Br-p)-C$_6$H$_4$-COOC$_2$H$_5$] *3 | " | 100.0 |
| [structure: 2-(NHCO-C$_6$H$_4$-Br-o)-C$_6$H$_4$-COOCH$_3$] *3 | " | 95.0 |
| [structure: 2-CH$_3$-C$_6$H$_4$-CONH-C$_6$H$_5$] *4 | " | 100.0 |
| [structure: 2-OH-C$_6$H$_4$-CONH-C$_6$H$_5$] *5 | " | 100.0 |
| [structure: C$_{13}$H$_{27}$-N(morpholine with 2,6-dimethyl)] *6 | 50 | 1.0 |
| | 10 | 37.5 |
| No treatment | — | 100.0 |

Note:
*1 Compound disclosed in J. Med. Chem., Vol. 11, 369 (1968)
*2 Compound disclosed in Can. J. Chem., Vol. 46, 2589 (1968)
*3 Compounds disclosed in Bull. soc. chim. France, 337 (1960)
*4 Commercially available fungicide: mebenil
*5 Commercially available fungicide: salicylanilide
*6 Commercially available fungicide: tridemorph

EXAMPLE 6

Protective activity test on powdery mildew of apple (*Podosphaera leucotricha*):

Apple seedlings (var. Kougyoku) were sprayed with an aqueous solution of each emulsifiable concentrate at a rate of 40 ml per plant. After the solution was air-dried, the test plants were inoculated with *Podosphaera leucotricha* and cultivated for 14 days under a fluorescent light at 20° C. Thereafter, rates of infection were assessed and percentages of disease severity were calculated in the same manner as in Example 3.

The test results are shown in Table 5. As is apparent from the results, the compounds of the present invention showed a more superior protection activity than the control compounds.

Table 5

| Compound No. | Concentration of active ingredient (ppm) | Disease severity (%) |
|---|---|---|
| 1 | 100 | 0.0 |
| 9 | " | 2.5 |

Table 5-continued

| Compound No. | Concentration of active ingredient (ppm) | Disease severity (%) |
|---|---|---|
| 14 | " | 0.0 |
| 23 | " | 5.0 |
| 24 | " | 0.0 |
| 40 | " | 0.0 |
| 48 | " | 2.5 |
| 51 | " | 5.0 |
| 2-NH₂-C₆H₄-COOC₄H₉(n) *1 | " | 72.5 |
| 2-NHCOCH₃-C₆H₄-COOCH₃ *2 | " | 85.0 |
| 2-(NHCO-C₆H₅)-C₆H₄-COOH *3 | " | 70.0 |
| 2-(NHCO-C₆H₄-4-CH₃)-C₆H₄-COOCH₃ *3 | " | 80.0 |
| 2-(NHCO-C₆H₄-4-Br)-C₆H₄-COOC₂H₅ *3 | " | 75.0 |
| 2-(NHCO-C₆H₄-2-Br)-C₆H₄-COOCH₃ *3 | " | 70.0 |
| 2-CH₃-C₆H₄-CONH-C₆H₅ *4 | " | 77.5 |
| 2-OH-C₆H₄-CONH-C₆H₅ *5 | " | 85.0 |
| 2,4-(NO₂)₂-6-(CH(CH₃)C₆H₁₃)-C₆H₂-OCOCH=CHCH₃ *6 | " | 22.5 |
| No treatment | — | 85.0 |

Note:
*1 Compound disclosed in J. Med. Chem., Vol. 11, 369 (1968)
*2 Compound disclosed in Can. J. Chem., Vol. 46, 2589 (1968)
*3 Compound disclosed in Bull. soc. chim. France, 337 (1960)
*4 Commercially available fungicide: mebenil
*5 Commercially available fungicide: salicylanilide
*6 Commercially available fungicide: dinocap

EXAMPLE 7

Protective activity test on powdery mildew of rose (*Sphaerotheca pannosa*)

Rose seedlings (var. Peace) in flower pots were sprayed with an aqueous solution of each emulsifiable concentrate at a rate of 30 ml per plant. After the solution was air-dried, the test plants were inoculated with *Sphaerotheca pannosa* and cultivated for 14 days in a green house. Thereafter, rates of infection were assessed and percentages of disease severity were calculated in the same manner as in Example 3.

The test results are shown in Table 6. As is apparent from the results, the compounds of the present invention showed a more superior protection activity than the control compounds.

Table 6

| Compound No. | Concentration of active ingredient (ppm) | Disease severity (%) |
|---|---|---|
| 1 | 100 | 0.0 |
| 12 | " | 5.0 |
| 17 | " | 0.0 |
| 31 | " | 0.0 |
| 45 | " | 0.0 |
| 51 | " | 0.0 |
| 2-NH₂-C₆H₄-COOC₄H₉(n) *1 | " | 65.0 |
| 2-NHCOCH₃-C₆H₄-COOCH₃ *2 | " | 62.5 |
| 2-(NHCO-C₆H₅)-C₆H₄-COOH *3 | " | 60.0 |
| 2-(NHCO-C₆H₄-4-CH₃)-C₆H₄-COOCH₃ *3 | " | 70.0 |
| 2-(NHCO-C₆H₄-4-Br)-C₆H₄-COOC₂H₅ *3 | " | 75.0 |

Table 6-continued

| Compound No. | | Concentration of active ingredient (ppm) | Disease severity (%) |
|---|---|---|---|
| 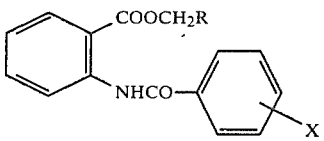 *3 | | " | 67.5 |
| *4 | | " | 72.5 |
| *5 | | " | 70.0 |
| 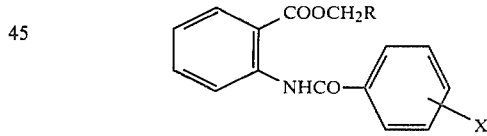 *6 | | " | 17.5 |
| No treatment | | — | 72.5 |

Note:
*[1] Compound disclosed in J. Med. Chem., Vol. 11, 369 (1968)
*[2] Compound disclosed in Can. J. Chem., Vol. 46, 2589 (1968)
*[3] Compound disclosed in Bull. soc. chim. France, 337 (1960)
*[4] Commercially available fungicide: mebenil
*[5] Commercially available fungicide: salicylanilide
*[6] Commercially available fungicide: dinocap

What is claimed is:

1. A method of killing phytopathogenic fungi which comprises contacting said fungi with a fungicidally effective amount of a N-benzoylanthranilate of the formula, wherein X is a hydrogen or 3-halogen atom or a 3-methoxy, 4-methoxy, 2,4-dimethoxy, 3,4-dimethoxy, 3-halo-4-methoxy, 3,4-methylenedioxy or 3,5-dimethoxy group and R is a hydrogen atom or a $C_1$–$C_7$ alkyl, $C_3$–$C_6$ cycloalkyl, $C_2$–$C_4$ alkenyl, halo-$C_1$–$C_3$ alkyl, $C_1$–$C_4$ alkoxy $C_1$–$C_4$ alkyl or N,N-di-$C_1$–$C_2$ alkylamino $C_1$–$C_4$ alkyl group, and an inert carrier.

2. The process according to claim 1, wherein X is a hydrogen, 3-fluorine, 3-chlorine, 3-bromine or 3-iodine atom or a 3-methoxy, 4-methoxy, 2,4-dimethoxy, 3,4-dimethoxy, 3-fluoro-4-methoxy, 3-chloro-4-methoxy, 3,4-methylenedioxy or 3,5-dimethoxy group and R is a hydrogen atom or a $C_1$–$C_7$ alkyl, cyclopropyl, vinyl, 2-methylvinyl, chloromethyl, methoxymethyl or N,N-dimethylaminomethyl group.

3. The process according to claim 1, wherein X is a hydrogen atom and R is a hydrogen atom or a methyl or vinyl group.

4. The process according to claim 1, wherein X is a 3-iodine atom and R is a methyl, ethyl, n-propyl, vinyl, chloromethyl or N,N-dimethylaminomethyl group.

5. The process according to claim 1, wherein X is a 4-methoxy group and R is an ethyl, i-propyl or vinyl group.

6. The process according to claim 1, wherein X is a 2,4-dimethoxy group and R is a n-propyl group.

7. The process according to claim 1, wherein X is a 3,4-dimethoxy group and R is a hydrogen atom or a methyl, ethyl, n-propyl, i-propyl, vinyl, methoxymethyl or N,N-dimethylaminomethyl group.

8. The process according to claim 1, wherein X is a hydrogen atom and R is a hydrogen atom.

9. The process according to claim 1, wherein X is a hydrogen atom and R is a vinyl group.

10. The process according to claim 1, wherein X is a 3-iodine atom and R is a n-propyl group.

11. The process according to claim 1, wherein X is a 4-methoxy group and R is an ethyl group.

12. The process according to claim 1, wherein X is a 4-methoxy group and R is a vinyl group.

13. The process according to claim 1, wherein X is a 3,4-dimethoxy group and R is a n-propyl group.

14. The process according to claim 1, wherein X is a 3,4-dimethoxy group and R is a vinyl group.

15. A method of killing phytopathogenic fungi which comprises contacting said fungi with a fungicidally effective amount of a N-benzoylanthranilate of the formula, wherein X is a 3,4-methylenedioxy group and R is a hydrogen atom or a methyl, ethyl, n-propyl or methoxymethyl group.

16. The process according to claim 1, wherein X is a 3,4-methylenedioxy group and R is an ethyl group.

17. The process according to claim 1, wherein X is a 3,4-methylenedioxy group and R is a n-propyl group.

18. The process according to claim 17, wherein X is a 3,4-methylenedioxy group and R is a methoxymethyl group.

* * * * *